United States Patent [19]

Schulte-Elte et al.

[11] Patent Number: 4,525,298
[45] Date of Patent: Jun. 25, 1985

[54] ALIPHATIC ALCOHOLS AND ESTERS AND THEIR USE AS PERFUMING INGREDIENTS

[75] Inventors: Karl H. Schulte-Elte, Onex; Bernard L. Muller, Geneva, both of Switzerland

[73] Assignee: Firmenich SA, Geneva, Switzerland

[21] Appl. No.: 442,676

[22] Filed: Nov. 18, 1982

[30] Foreign Application Priority Data

Dec. 7, 1981 [CH] Switzerland .................. 7791/81

[51] Int. Cl.³ .................. C07C 69/24; C11B 9/00
[52] U.S. Cl. .................. 252/522 R; 252/174.11; 424/70; 560/261; 560/265; 560/266; 568/902
[58] Field of Search .................. 252/522 R, 174.11; 560/261, 265, 266; 568/902; 424/70

[56] References Cited

U.S. PATENT DOCUMENTS 4,406,810  9/1983  Boden .................. 252/522 R

FOREIGN PATENT DOCUMENTS 2108805  2/1970  Fed. Rep. of Germany ... 252/522 R

OTHER PUBLICATIONS

Arctander, *Perfume and Flavor Chemicals*, Monograph 3007-3008, (1967).
Blumenthal, Jack H., α-Methylene and α-Methyl Aldehydes and Alcohols, Chemical Abstracts, vol. 70, No. 37191j, 1969.

*Primary Examiner*—Thomas A. Waltz
*Attorney, Agent, or Firm*—Pennie & Edmonds

[57] ABSTRACT

There are disclosed compounds of formula

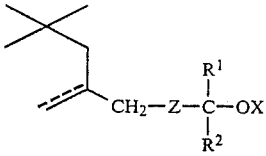

(I)

having a single or a double bond in the position indicated by the dotted line and wherein:

Z represents an ethylene, ethenyl or an ethynyl divalent radical;

X represents a hydrogen atom or an acyl radical, derived from a linear or branched lower hydrocarbon of formula R—CO, wherein R designates a hydrogen atom or a lower alkyl group, and $R^1$ and $R^2$, identical or different, represent each a hydrogen atom or a linear or branched alkyl radical.

Compounds (I) possess useful perfuming properties.

3 Claims, No Drawings

ALIPHATIC ALCOHOLS AND ESTERS AND THEIR USE AS PERFUMING INGREDIENTS

BRIEF SUMMARY OF THE INVENTION

The instant invention relates to compounds of formula

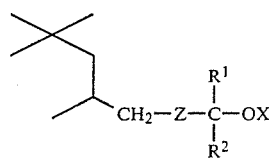

(I)

having a single or a double bond in the position indicated by the dotted line and wherein:

Z represents an ethylene, ethenyl or an ethynyl divalent radical;

X represents a hydrogen atom or an acyl radical, derived from a linear or branched lower hydrocarbon of formula R—CO, wherein R designates a hydrogen atom or a lower alkyl group, and $R^1$ and $R^2$, identical or different, represent each a hydrogen atom or a linear or branched alkyl radical.

This invention provides also a process to confer, improve or modify the fragrance properties of perfumes and perfumed products which process comprises the step of adding thereto a fragrance modifying quantity of a compound of formula (I).

The invention provides further a perfume composition containing as active ingredient a compound of formula (I).

BACKGROUND OF THE INVENTION

The prior art discloses a certain number of compounds possessing a vague structural relationship to compounds (I) of the present invention. The following are worth of mention:

a.

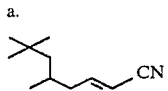  5,7,7-trimethyl-oct-2-ene-nitrile (U.S. Pat. No. 3,531,510)

b.

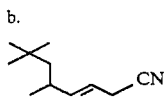  5,7,7-trimethyl-oct-3-ene-nitrile (U.S. Pat. No. 3,531,510)

c.

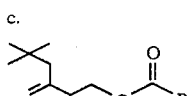  esters of 3-methylene-5,5-dimethyl-hexanol (DE-OS 2,108,805)

d.

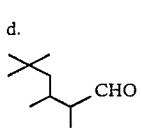  aldehyde TMH (origin: Dragoco, Holzminden, Germany)

Compounds a. and b. possess an odor that is reminiscent of clove or orris-like and develop earthy, fresh and green notes. Ester c. possesses an odor which, depending on substituent R, varies from minty to flowery, orris-like, fruity or woody. Aldehyde TMH possesses a fresh, green, aldehydic smell reminiscent of herbs, flowers and ozone.

We have now discovered that compounds (I) develop particularly useful fragrance properties that are distinct from those of the prior known analogs. Due to their odor characteristics, they find a utility in conferring, improving or modifying the odorous notes of fruity type, especially of pear-like type, or of ambrette, woody, flowery and balsamic type.

PREFERRED EMBODIMENTS OF THE INVENTION

Preferred compounds of formula (I) include those compounds wherein $R^1$ and $R^2$ represent each an alkyl group of $C_1$ to $C_6$, especially a methyl, an ethyl, a propyl or an isopropyl radical. Among the acid compounds, 5,7,7-trimethyl-octyl propionate is a particularly valuable product whose fruity, peak-like note is especially interesting. Due to its good stability towards acidic reagents, oxidants and other current constituents in the different media of use, the said ester can be conveniently utilized to perfume articles of various nature such as soaps, shampoos, lipsticks and powder and liquid detergents.

To this end, compounds (I) can be used at concentrations varying in a wide range of values. Thus, concentrations of the order of about 1% parts by weight, based on the weight of the composition in which they are incorporated can already achieve a marked effect. These concentrations can be as high as 20 or even 30%, namely in the manufacture of perfume concentrates or "coeurs". It is understood by the experts in the art that the concentration values can be much lower whenever compounds (I) are used to perfume articles such as, for example, soaps or cosmetics. Typical compounds of formula (I) include the following.

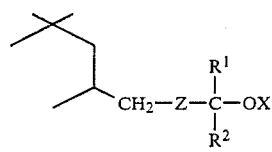

(I)

TABLE I

| | Z = —CH$_2$—CH$_2$— | | |
|---|---|---|---|
| | R | $R^1$ | $R^2$ |
| X = R—CO | | | |
| 1. | C$_2$H$_5$— | H | H |
| 2. | H | H | H |
| 3. | CH$_3$ | H | H |
| 4. | iso-C$_3$H$_7$ | H | H |
| X = H | | | |
| 5. | | CH$_3$ | H |
| 6. | | CH$_3$ | CH$_3$ |
| 7. | | CH$_3$ | iso-C$_3$H$_7$ |
| 8. | | C$_3$H$_7$ | H |
| 9. | | C$_2$H$_5$ | CH$_3$ |
| 9b. | | H | H |

TABLE II

| | R | R¹ | R² |
|---|---|---|---|
| Z = —CH=CH— | | | |
| X = R—CO | | | |
| 10. | H | H | H |
| 11. | CH₃ | H | H |
| 12. | C₃H₇ | H | H |
| 13. | H | CH₃ | H |
| 14. | CH₃ | CH₃ | H |
| 15. | C₂H₅ | CH₃ | H |
| X = H | | | |
| 16. | | H | H |
| 17. | | CH₃ | CH₃ |
| 18. | | CH₃ | H |
| 19. | | iso-C₃H₇ | CH₃ |
| 20. | | C₃H₇ | H |
| 21. | | C₂H₅ | H |
| 22. | | C₂H₅ | C₂H₅ |

TABLE III

| | R | R¹ | R² |
|---|---|---|---|
| Z = —CH≡CH— | | | |
| X = R—CO | | | |
| 23. | C₂H₅ | H | H |
| 24. | CH₃ | H | H |
| 25. | H | H | H |
| X = H | | | |
| 26. | | H | H |
| 27. | | CH₃ | H |
| 28. | | CH₃ | CH₃ |
| 29. | | CH₃ | iso-C₃H₇ |
| 30. | | C₃H₇ | H |
| 31. | | C₂H₅ | CH₃ |
| 32. | | C₂H₅ | C₂H₅ |
| 33. | | C₂H₅ | H |

The compounds defined in Tables I to III have been prepared as follows (temperature in degrees centigrade).

1. 5,7,7-Trimethyloctyl propionate

The process for the preparation of this compound can be illustrated according to the following reaction scheme:

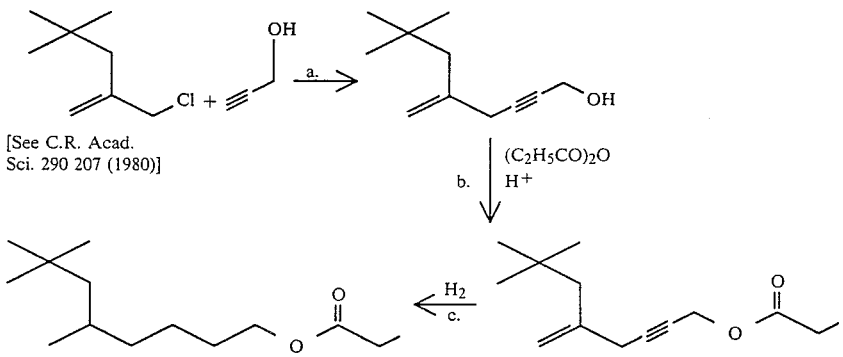

[See C.R. Acad. Sci. 290 207 (1980)]

a. 11.2 g (0.2M) of prop-1-yn-3-ol, 1.0 g of hydroxylamine hydrochloride and 1.4 g of $Cu_2Cl_2$ have been added to a solution of 14.6 g of KOH (0.26M) in 80 ml of ethanol. The resulting mixture has been stirred vigorously for 10 minutes, then 87.9 g of 2-chloro-methyl-4,4-dimethyl-pent-1-ene of technical grade (0.4M of pure product) were added thereto. The addition was exothermic and the mixture was kept at 25°–32° during the whole operation (45 min), while the stirring was maintained overnight. The resulting reaction mixture was taken up with 30°–50° petrol ether, washed successively with water, 10% HCl and with water again until neutrality. After drying and evaporation, the obtained residue was distilled to give 16.6 g of 5-(2,2-dimethylpropyl)-5-hexen-2-yn-1-ol (yield 45%).

IR: 3320, 3080, 1640 and 910 cm⁻¹;
NMR: 0.92 (9H, s); 2.0 (2H, s); 2.98 (2H, s); 4.31 (2H, s); 4.82 (s) and 5.22 (m) (2H) δ ppm;
MS: M⁺=166(0.1); m/e: 151(1), 133(3), 123(1), 105(2), 91(11), 79(2), 67(1), 57(100), 41(24), 39(7).

b. 3.32 g (20 mM) of 5-(2,2-dimethylpropyl)-5-hexen-2-yn-1-ol have been esterified by means of 4.5 g (35 mM) of propionic anhydride and 0.2 ml of concentrated $H_3PO_4$. The mixture was taken up with ether, then it was washed with 2 fractions of a 2N solution of NaOH, neutralized with water, dried and concentrated. Bulb distillation at 6.65 Pa gave 4.4 g of 5-(2,2-dimethylpropyl)-5-hexen-2-ynyl propionate (yield 70%).

IR: 3080, 2250, 1740, 1640 and 910 cm⁻¹;
NMR: 0.9(9H, s); 1.98(2H, s); 2.10–2.55 (2H, m); 2.98(2H, s); 4.7 (2H, m); 4.82 and 5.22 (2H, s and m) δ ppm;
MS: M⁺=222(0.1); m/e: 205(0.1), 179(0.1), 166(10), 151(4), 133(11), 123(2), 110(21), 92(21), 91(45), 77(3), 65(2), 57(100), 41(22).

c. 1.11 g (5 mM) of 5-(2,2-dimethylpropyl)-5-hexen-2-ynyl propionate in 50 ml ethanol were hydrogenated in the presence of 0.4 g of 10% palladium on charcoal. After adsorption of the theoretical amount of hydrogen, the mixture was filtered over diatomaceous earth, concentrated and bulb distilled (13.3 Pa) to give 0.85 g of 5,7,7-trimethyloctyl propionate (yield 80%).

IR: 1740 cm⁻¹;
NMR (60 MHz; CDCl₃): 0.90(9H, s); about 0.91 (3H, d, J=6 Hz); 3.47 (2H, q, J=7 Hz); 4.1 (2H, t, J=6 Hz) δ ppm;
MS: m/e: 213(1), 173(1), 139(2), 126(0), 111(1), 98(18), 83(32), 75(40), 57(100), 41(19).

1. 5-Methylene-7,7-dimethyl-octyl propionate 20 mM of 5-methylene-7,7-dimethyl-octanol were mixed at room temperature under nitrogen with 4 ml of propionic anhydride and some drops of concentrated $H_3PO_4$. The mixture was taken up with ether, washed with a 2N NaOH solution, then with water until neutrality. After drying, concentration and bulb distillation the desired ester was obtained in 89%.

IR: 3080, 1760, 1640, 900 cm⁻¹;

NMR: 0.91 (9H, s); 1.92 (2H, s); 3.94–4.22 (2H, m); 4.71 and 4.83 (2H, m) δ ppm;

MS: M+ =226(≧0.1); m/e: 152(7), 137(3), 123(0.5), 109(1), 96(56), 81(36), 68(13), 57(100), 41(29), 29(36).

This ester possesses a fruity odor of pear-type.

2. 5,7,7-Trimethyl-octyl formate (see the process for the preparation of the corresponding propionate ester).

IR: 1720 cm$^{-1}$;

NMR (60 MHz; CDCl$_3$): 0.88 (9H, s); 0.92 (3H, d); 4.19 (2H, t, J=6 Hz); 8.05 (1H, s) δ ppm;

MS: m/e: 145(1), 99(5), 83(19), 69(7), 57(100), 56(31), 41(19), 29(7).

Flowery odor.

2. 5-Methylene-7,7-dimethyl-octyl formate 20 mM of 5-methylene-7,7-dimethyloctanol were esterified with 6 ml of concentrated formic acid. The reaction took place at room temperature, under nitrogen and by mixing the ingredients under stirring for 24 h. The mixture was taken up with ether, washed with 2N NaOH, then with water until neutrality. The desired product was obtained after drying, concentration and bulb distillation under reduced pressure.

IR: 3080, 1720, 1640, 900 cm$^{-1}$;

NMR: 0.91 (9H, s); 1.93 (2H, s); 4.03–4.31 (2H, m); 4.65–4.91 (2H, m); 8.04 (1H, s) δ ppm;

MS: M+ −198(1); m/e: 183(1), 165(0.1), 152(1), 142(1), 123(0.1), 109(1), 96(25), 81(18), 68(6), 57(100), 41(27).

3. 5,7,7-Trimethyl-octyl acetate (see the process for the preparation of the corresponding propionate)

IR: 1740 cm$^{-1}$;

NMR (60 MHz; CDCl$_3$): 0.88 (9H, s); 0.90 (3H, d); 2.03 (3H, s); 4.08 (2H, t, J=6 Hz) δ ppm;

MS: m/e: 159(s), 139(2), 111(1), 98(21), 83(40), 69(20), 57(100), 56(44), 41(43), 29(11).

3. 5-Methylene-7,7-dimethyl-octyl acetate

IR: 3080, 1740, 1640, 900 cm$^{-1}$;

NMR: 0.91 (9H, s); 2.04 (3H, s); 3.92–4.20 (2H, m); 4.65–4.90 (2H, m) δ ppm;

MS: M+ =212(≧0.1); m/e: 152(9), 137(3), 123(0.1), 109(1), 96(70), 81(42), 68(20), 57(100), 43(43).

Flowery odor.

4. 5,7,7-Trimethyl-octyl isobutyrate

IR: 1740 cm$^{-1}$;

NMR (60 MHz, CDCl$_3$): 0.89 (9H, s); 0.92 (3H, d, J=4 Hz); 1.19 (6H, d, J=7 Hz); 2.3–2.8 (1H, m); 4.09 (2H, t, J=6 Hz) δ ppm;

MS: m/e: 186(3), 139(1), 111(1), 98(19), 89(59), 71(24), 57(100), 56(84), 43(39).

5. 6,8,8-Trimethyl-2-nonanol

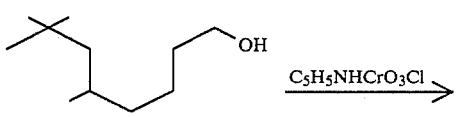

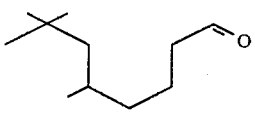

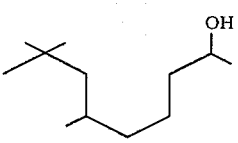

IR: 3320 cm$^{-1}$;

NMR: 0.98 (9H, s); 1.21 (3H, d, J=6 Hz); 3.68–4.05 (1H, m) δ ppm;

MS: M+ =186(≧0.1); m/e: 171(1), 153(1), 141(0.1), 129(1), 112(15), 97(18), 83(16), 69(19), 56(100), 41(22).

6. 2,6,8,8-Tetramethyl-2-nonanol

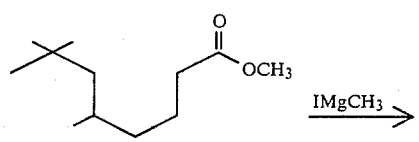

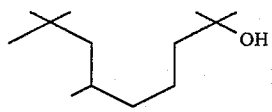

IR: 3350 cm$^{-1}$;

NMR (60 MHz, CDCl$_3$): 0.88 (9H, s); 0.92 (3H, d); 1.22 (6H, s) δ ppm;

MS: m/e: 185(1), 126(1), 111(5), 97(3), 83(2), 69(13), 59(100), 57(32), 41(8), 29(3). Green and herbaceous odor.

7. 2,3,7,9,9-Pentamethyl-3-decanol

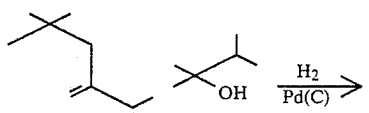

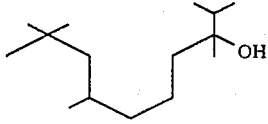

IR: 3350 cm$^{-1}$;

NMR: 0.88 (9H, s); 1.08 (3H, s) δ ppm;

MS: M+ =228(≧0.1); m/e: 213(0.1), 185(3), 167(1), 154(2), 139(0.5), 125(2), 111(8), 97(5), 87(39), 71(20), 57(100), 43(26), 29(9).

Slightly flowery odor.

8. 8,10,10-Trimethyl-4-undecanol

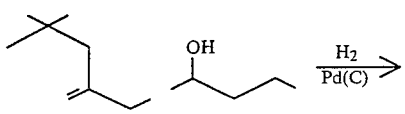

IR: 3330 cm$^{-1}$;

NMR: 0.89 (9H, s); 0.9 (3H, d); 3.42–3.78 (H, m) δ ppm;

MS: m/e: 196(0.1), 181(0.1), 171(2), 153(0.1), 140(8), 125(2), 115(11), 97(18), 83(17), 69(20), 57(100), 56(25), 55(36), 41(23).

Balsamic and flowery odor.

9. 3,7,9,9-Tetramethyl-3-decanol

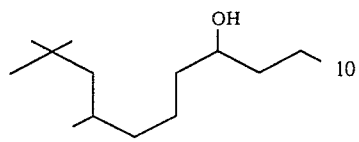

IR: 3340 cm$^{-1}$;

NMR: 0.88 (9H, s); 1.10 (3H, s) δ ppm;

MS: M$^+$=214(≧0.1); m/e: 192(7), 181(9), 163(6), 135(39), 125(15), 107(51), 93(15), 79(14), 69(11), 57(100), 43(44).

Flowery-fruity, slightly woody odor.

9b. 5,7,7-Trimethyl-octanol

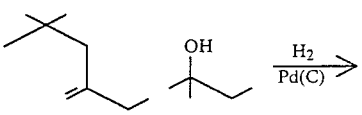

IR: 3300 cm$^{-1}$;

NMR (60 MHz): 0.91 (9H, s); about 0.92–0.93 (3H, d, J=about 6 Hz); 3,67 (2H, t, J=6 Hz) δ ppm;

MS: m/e: 157(1), 115(3), 97(7), 83(16), 69(7), 57(100), 41(21), 29(7).

10. 5-Methylene-7,7-dimethyl-oct-2-enyl formate

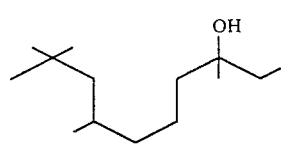

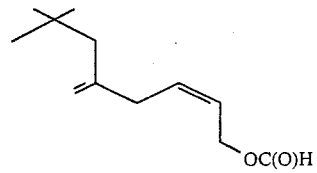

IR: 3080, 1730, 1640, 900 cm$^{-1}$;

NMR: 0.92 (9H, s); 1.96 (2H, s); 2.77–2.94 (2H, m); 4.61–4.92(4H, m); 5.56–5.81 (2H, m); 8.08 (H, s) δ ppm;

MS: M$^+$=196(0.1); m/e: 183(0.1), 164(0.1), 150(3), 135(3), 121(0,1), 107(2), 94(25), 79(35), 67(2), 57(100), 41(37).

Slightly fruity odor.

11. 5-Methylene-7,7-dimethyl-oct-2-enyl acetate

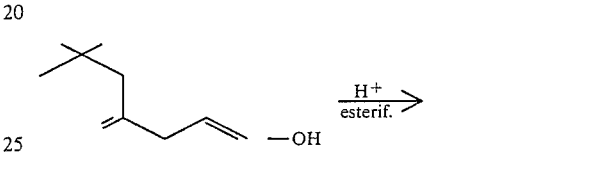

IR: 3080, 1740, 1640, 900 cm$^{-1}$;

NMR: 0.92 (9H, s); 1.97 (2H, s); 2.06 (3H, s); 2.78–2.98 (2H, m); 4.56–4.96(4H, m); 5.57–5.83 (2H, m) δ ppm;

MS: M$^+$=210 (≧0.1); m/e: 168(0.5), 150(5), 135(7), 121(0.5), 107(4), 94(59), 79(66), 67(4), 57(100), 43(47).

12. 5-Methylene-7,7-dimethyl-oct-2-enyl propionate

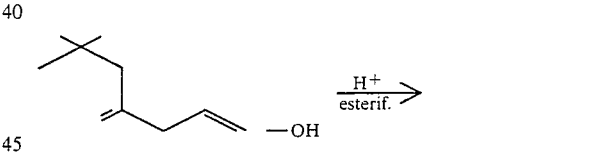

IR: 3080, 1740, 1640, 900 cm$^{-1}$;

NMR: 0.91 (9H, s); 1.92 (2H, s); 2.10–2.55 (2H, m); 2.70–2.94 (2H, m); 4.52–4.95 (4H, m); 5.31–5.74 (2H, m) δ ppm;

MS: M$^+$=228(≧0.1); m/e: 168(0.1), 150(5), 135(13), 121(0.5), 107(10), 94(44), 79(2.5), 67(2), 57(100), 41(27).

Fruity odor of pear-type.

13. 6-Methylene-8,8-dimethyl-non-3-en-2-yl formate

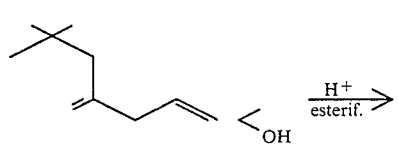

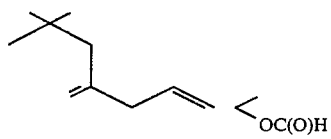

IR: 3080, 1730, 1640, 900 cm$^{-1}$;

NMR: 0.91 (9H, s); 1.35 (3H, d, J=7 Hz); 1.92 (2H, s); 2.68–2.88 (2H, m); 4.72–4.93 (2H, m); 5.30–5.68 (3H, m); 8.03 (H, s) δ ppm;

MS: M$^+$=210(≧0.1); m/e: 191(0.1), 164(6), 149(1), 135(0.1), 121(1), 108(15), 93(30), 79(10), 67(2), 57(100), 46(29), 41(36).

Multiodorant compound.

14. 6-Methylene-8,8-dimethyl-non-3-en-2-yl acetate

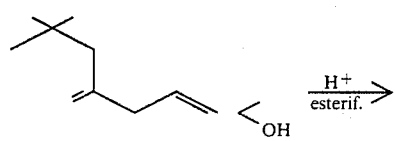

IR: 3080, 1740, 1640, 900 cm$^{-1}$;

NMR: 0.92 (9H, s); 1.27 (3H, d, J=7 Hz); 1.96 (2H, s); 2.0 (3H, s); 2.89–2.99 (2H, m); 4.68–4.92 (2H, m); 5.35–5.76 (3H m) δ ppm;

MS: M$^+$=224(≧0.1); m/e: 182(0.5), 164(10), 169(6), 135(1), 121(3), 108(45), 93(74), 79(25), 71(9), 57(100), 43(65).

Multiodorant compound.

15. 6-Methylene-8,8-dimethyl-non-3-en-2-yl propionate

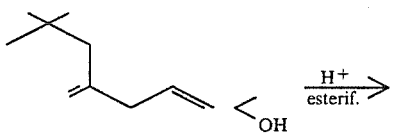

IR: 3080, 1740, 1640, 900 cm$^{-1}$;

NMR: 0.93 (9H, s); 1.31 (3H, d, J=6 Hz); 1.97 (2H, s); 2.07–2.56 (2H, m); 2.78–2.98 (2H, m); 4.68–4.93 (2H, m); 5.36–5.72 (3H, m) δ ppm;

MS: M$^+$=238(≧0.1); m/e: 182(0.5), 164(7), 149(4), 135(1), 121(2), 108(34), 93(54), 79(16), 68(5), 57(100), 41(28).

Fruity odor of pear-type.

16. 5-Methylene-7,7-dimethyl-oct-2-enol (cis and trans)

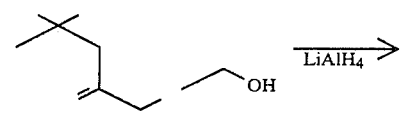

IR: 3310, 3080, 1640, 980 and 900 cm$^{-1}$;

NMR: 0.92 (9H, s); 1.93 (2H, s); 2.72–2.92 (2H, m); 4.01–4.4(2H, m); 4.72–4.93 (2H, m); 5.57–5.81 (2H, m) δ ppm;

MS: M$^+$=168(0.1); m/e: 150(0.1), 135(1), 123(0.1), 112(1), 94(13), 79(32), 67(1), 57(100), 41(28).

The corresponding cis isomer was obtained by reduction of the same alcohol by means of Lindlar catalyst.

IR: 3320, 3080, 1640 and 900 cm$^{-1}$;

NMR: 0.92 (9H, s); 1.97 (2H, s); 1.76–1.92 (2H, m); 4.12–4.28 (2H, m); 4.68–4.91 (2H, m); 5.21–5.80 (2H, m) δ ppm;

MS: M$^+$=168(0.1); m/e: 150(1), 135(1), 121(0,1), 107(1), 94(28), 79(37), 67(1), 57(100), 41(31).

17. 6-Methylene-2,8,8-trimethyl-non-3-enol (cis and trans)

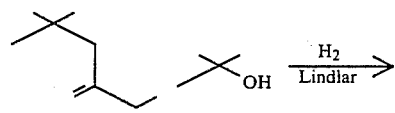

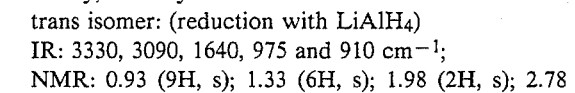

cis isomer:

IR: 3330, 3090, 1640 and 910 cm$^{-1}$;

NMR: 0.92 (9H, s); 1.36 (6H, s); 1.98 (2H, s); 3.11 (2H, d, J=3 Hz); 4.75(s) and 4.87(m) (2H); 5.12–5.71 (2H, m) δ ppm;

MS: M$^+$=196(0.1); m/e: 178(7), 163(4), 149(0.1), 135(0.5), 121(56), 107(60), 93(15), 79(11), 69(10), 57(100), 41(35), 29(21).

Fruity, flowery odor.

trans isomer: (reduction with LiAlH$_4$)

IR: 3330, 3090, 1640, 975 and 910 cm$^{-1}$;

NMR: 0.93 (9H, s); 1.33 (6H, s); 1.98 (2H, s); 2.78 (2H,d,J=2 Hz); 4.73(s) and 4.85(m) (2H); 5.51–5.71 (2H, m) δ ppm;

MS: M$^+$=196(≦0.1); m/e: 181(3), 163(1), 153(0.1), 138(1), 122(24), 107(39), 93(12), 82(10), 69(8), 57(100), 43(40), 41(31), 29(17).

Woody odor.

18. 6-Methylene-8,8-dimethyl-non-3-en-2-ol, (cis and trans)

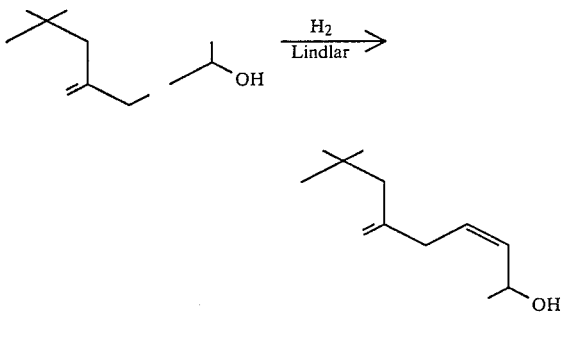

IR: 3330, 3090, 1640 and 910 cm$^{-1}$;

NMR: 0.91 (9H, s); 1.21 (3H, d, J=3 Hz); 1.94 (2H, s); 2.81 (2H,d), 4.32–4.68 (1H, m); 4.69–4.88 (2H, m); 5.32–5.62 (2H, m) δ ppm;

MS: M$^+$=182(0.1); m/e: 164(2), 149(1), 135(0.1), 121(1), 108(27), 93(46), 71(6), 57(100), 41(31), 29(19).

The corresponding trans derivative was obtained by reduction of the same acetylenic alcohol with LiAlH$_4$.

IR: 3330, 3080, 1640, 900 cm$^{-1}$;

NMR: 0.92 (9H, s); 1.27 (3H, d, J=7 Hz); 1.92 (2H, s); 2.68–2.92 (2H, m); 4.18–4.52 (H, m); 4.68–4.92 (2H, m); 5.49–5.70 (2H, m) δ ppm;

MS: M$^+$=182(0.1); m/e: 164(0.5), 149(1), 137(0.1), 123(1), 108(28), 93(42), 79(16), 71(14), 57(100), 41(29), 29(18).

Flowery odor.

19. 7-Methylene-2,3,9,9-tetramethyl-dec-4-en-3-ol (cis and trans)

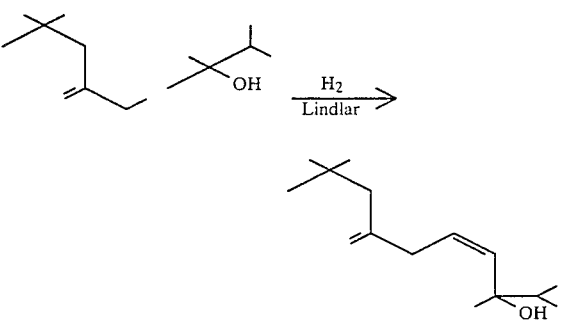

IR: 3450, 3090, 1640, 910 cm$^{-1}$;

NMR: 0.92 (9H, s); 0.92 (6H, d, J=2 Hz); 1.28 (3H, s); 1.98 (2H, s); 3.12 (2H, m); 5.15–5.70 (2H, m) δ ppm;

MS: M$^+$=224(<0.1); m/e: 206(4), 191(1), 181(22), 163(15), 149(1), 135(3), 125(29), 107(41), 93(10), 79(15), 71(11), 57(100), 43(61), 41(34), 29(17).

Woody odor, quince jam.

The corresponding trans isomer was obtained by reduction of the same acetylenic alcohol with LiAlH$_4$.

IR: 3330, 3090, 1640, 990 and 910 cm$^{-1}$;

NMR: 0.92 (9H, s), 1.28 (3H, s); 1.98 (2H, s); 4.73(s) and 4.86(m) (2H); 5.51–5.71 (2H, m) δ ppm;

MS: M$^+$=224(<0.1); m/e: 206(2), 191(0.5), 181(46), 163(4), 149(1), 135(6), 125(31), 107(30), 97(12), 83(13), 71(27), 57(100), 43(85), 41(48), 31(31).

Fruity, woody odor.

20. 8-Methylene-10,10-dimethyl-undec-5-en-4-ol (cis and trans)

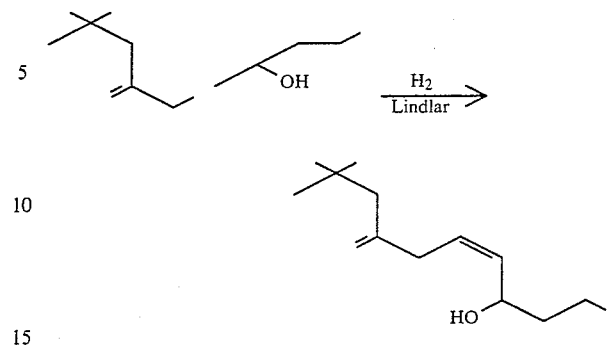

IR: 3330, 3080, 1640, 900 cm$^{-1}$;

NMR: 0.92 (9H, s); 1.98 (2H, s); 2.77–2.93 (2H, m); 4.20–4.61 (H, m); 4.68–4.96 (2H, m); 5.41–5.69 (2H, m) δ ppm;

MS: M$^+$=210(0.1); m/e: 192(3), 177(1), 167(1), 149(2), 136(14), 121(7), 107(13), 93(44), 79(16), 71(15), 57(100), 43(22), 41(33).

Woody odor.

The corresponding trans isomer was obtained by reduction of the same acetylenic alcohol with LiAlH$_4$.

IR: 3330, 3080, 1640, 990 and 900 cm$^{-1}$;

NMR: 0.92 (9H, s); 1.94 (2H, s); 2.70–2.86 (2H, s); 3.90–4.28 (H, m); 4.68–4.92 (2H, m); 5.47–5.71 (2H, m) δ ppm;

MS: M$^+$=210(0.1); m/e: 192(0.5), 177(0.5), 167(2), 149(2), 136(9), 121(9), 107(14), 93(34), 79(17), 71(19), 57(100), 43(20), 41(29).

21. 7-Methylene-3,9,9-trimethyl-dec-4-en-3-ol

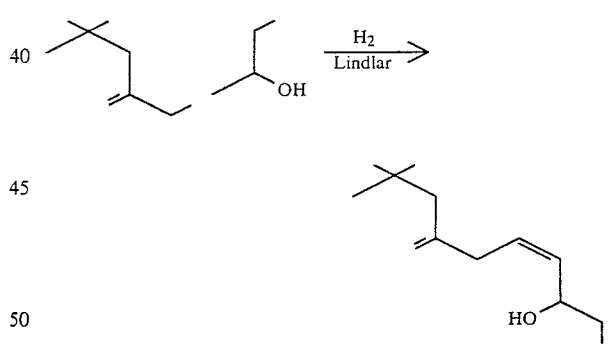

IR: 3330, 3090, 1640 and 910 cm$^{-1}$;

NMR: 0.92 (9H, s); 1.96 (2H, s); 2.83 (2H, d, J=3 Hz); 4.21–4.53 (1H, m); 4.75(s) and 4.87(m) (2H); 5.12–5.75 (2H, m) δ ppm;

MS: M$^+$=196(0.1); m/e: 178(4), 163(1), 149(2), 140(0,5), 122(17), 107(16), 93(49), 79(16), 69(8), 57(100), 41(38), 29(31).

22. 7-Methylene-9,9-dimethyl-3-ethyl-dec-4-en-3-ol

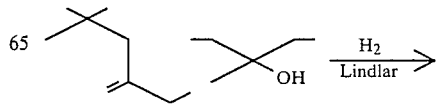

-continued

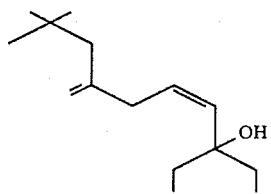

IR: 3460, 3080, 1640, 900 cm$^{-1}$;

NMR: 0.92 (9H, s); 1.98 (2H, s); 3.01–3.23 (2H, m); 4.70–4.97 (2H, m); 5.37–5,65 (2H, m) δ ppm;

MS: M$^+$=224(≧0,1); m/e: 206(9), 195(16), 177(9), 167(0,5), 149(0,5), 149(25), 139(19), 121(31), 107(12), 93(10), 79(12), 69(7), 57(100), 41(26). 23. 5-Methylene-7,7-dimethyl-oct-2-yn-1-yl propionate

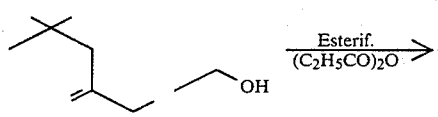

IR: 3080, 2250, 1740, 1640 and 910 cm$^{-1}$;

NMR: 0.9 (9H, s); 1.98 (2H, s); 2.10–2.55 (2H, m); 2.98(2H, s); 4.7 (2H, m); 4.82(s) and 5.22(m) (2H) δ ppm;

MS: M$^+$=222(0.1); m/e: 205(0.1), 179(0.1), 166(10), 151(4), 133(11), 123(2), 110(21), 92(21), 91(45), 77(3), 65(2), 57(100), 41(22).

Vegetable, spicy odor.

24. 5-Methylene-7,7-dimethyl-oct-2-yn-1-yl acetate

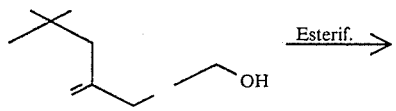

IR: 3080, 2240, 1740, 1640, 900 cm$^{-1}$;

NMR: 0.92 (9H, s); 1.98 (2H, s); 2.07 (3H, s); 2.98 (broad s); 4.62–4.75 (2H, m); 4.83–5.12 (2H, m) δ ppm;

MS: M$^+$=208(0.1); m/e: 193(0.1), 166(2), 152(13), 133(8), 123(2), 120(45), 91(71), 77(3), 65(3), 57(100), 43(44).

25. 5-Methylene-7,7-dimethyl-oct-2-yn-1-yl formate

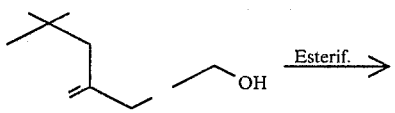

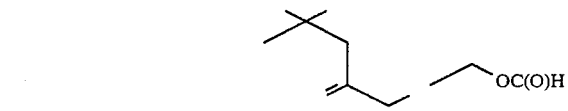

IR: 3080, 2240, 1730, 1640, 900 cm$^{-1}$;

NMR: 0.92 (9H, s); 2.0 (2H, s); 3.0 (2H, broad s); 4.72–4.88 (3H, m); 5.22 (H, m); 8.06 (H, s) δ ppm;

MS: M$^+$=194(0.1); m/e: 179(0.1), 165(0.1) 151(1), 133(6), 123(1), 105(3), 91(20), 77(2), 65(1), 57(100), 41(22).

26. 5-Methylene-7,7-dimethyl-oct-2-yn-1-ol

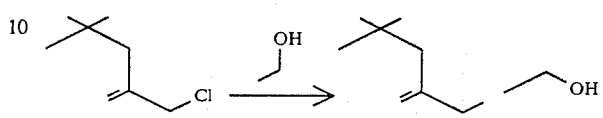

IR: 3320, 3080, 2250, 1640 and 910 cm$^{-1}$;

NMR: 0.92 (9H, s); 2.0 (2H, s); 2.98 (2H, s); 4.31 (2H, s); 4.82(s) and 5.22(m) δ ppm;

MS: M$^+$=166(0.1); m/e: 151(1), 133(3), 123(1), 105(2), 91(11), 79(2), 67(1), 57(100), 41(24), 39(7).

Multiodorant compound.

27. 6-Methylene-8,8-dimethyl-non-3-yn-2-ol

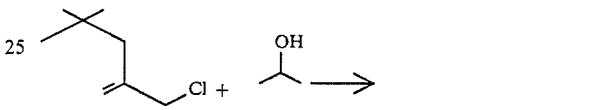

IR: 3320, 3080, 2250, 1640 and 910 cm$^{-1}$;

NMR: 0.92 (9H, s); 1.45 (3H, d, J=3 Hz); 2.0 (2H, s); 2.98 (2H, m); 4.35–4.68 (1H, m); 4.81 and 5.21 (2H, m) δ ppm;

MS: M$^+$=180(0.1); m/e: 165(0.2), 147(6), 133(0.1), 119(0.5), 106(16), 91(39), 79(3), 66(2), 57(100), 43(18), 41(27), 29(18).

28. 6-Methylene-2,8,8-trimethyl-non-3-yn-2-ol

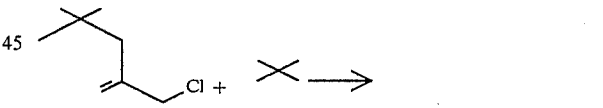

IR: 3350, 3080, 2250, 1640, 900 cm$^{-1}$;

NMR: 0.92 (9H, s); 1.52 (6H, s); 2.0 (2H, s); 2.97 (2H, s); 4.82(s) and 5.21(m) (2H) δppm;

MS: M$^+$=194(≧0.1); m/e: 179(0.1), 161(1), 133(1), 120(39), 105(35), 91(6), 80(8), 67(2), 57(100), 43(31), 29(19).

Fruity odor.

29. 7-Methylene-2,3,9,9-tetramethyl-dec-4-yn-3-ol

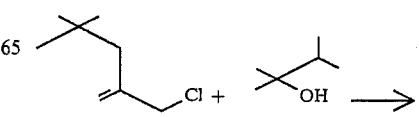

-continued

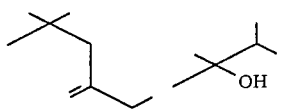

IR: 3400, 3080, 2250, 1640, 910 cm$^{-1}$;
NMR: 0.91 (9H, s); 1.07 (6H, d); 1.47 (3H, s); 2.0 (2H, s); 2.98 (2H, m); 4.81(s) and 5.21(m) (2H) δ ppm;
MS: M$^+$=222($\leq$0.1); m/e: 204(0.5), 189(0.5), 179(47), 165(1), 151(3), 133(18), 123(99), 105(9), 91(6), 79(4), 69(6), 57(100), 43(87), 29(19).
Woody, fruity odor.

30. 8-Methylene-10,10-dimethyl-undec-5-yn-4-ol

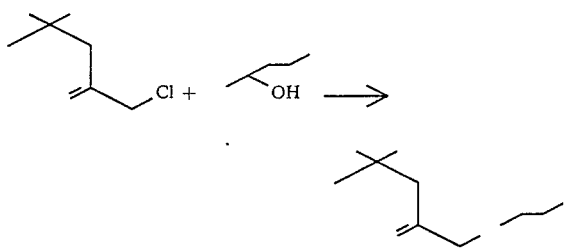

IR: 3320, 3080, 2250, 1640 and 910 cm$^{-1}$;
NMR: 0.91 (9H, s); 2.0 (2H, s); 2.98 (2H, m); 4.45 (1H, m); 4.81(s) and 5.21(m) (2H) δppm;
MS: M$^+$=208(0.1); m/e: 193(1), 175(3), 147(1), 134(15), 119(18), 106(22), 105(20), 91(18), 79(11), 71(5), 57(100), 41(31).

31. 7-Methylene-3,9,9-trimethyl-dec-4-yn-3-ol

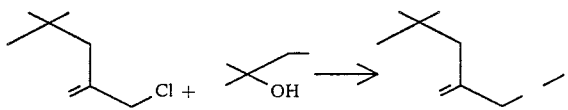

IR: 3350, 3080, 2250, 1640, 900 cm$^{-1}$;
NMR: 0.92 (9H, s); 1.49 (3H, s); 2.0 (2H, s); 2.98 (2H, s); 4.81(s) and 5.22(m) (2H) δ ppm;
MS: M$^+$=208(0.1); m/e: 193(0.1), 179(24), 161(0.5), 151(0.5), 134(50), 123(44), 105(13), 91(7), 79(7), 73(8), 57(100), 43(56), 29(24).
Flowery odor.

32. 7-Methylene-9,9-dimethyl-3-ethyl-dec-4-yn-3-ol

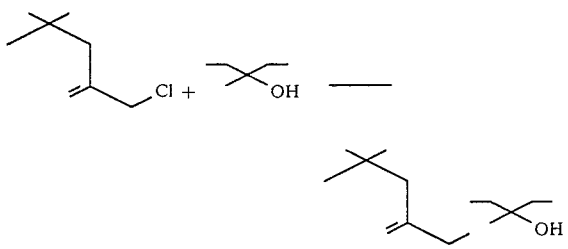

IR: 3370, 3080, 2240, 1640, 990 cm$^{-1}$;
NMR: 0.93 (9H, s); 2.0 (2H, s); 3.0 (2H, s); 4.82(s) and 5.22(m) (2H) δ ppm;
MS: M$^+$=222(0.1); m/e: 204(0.1), 193(34), 175(0.1), 161(0.1), 161(0.1), 148(20), 137(63), 119(8), 105(3), 91(5), 79(3), 69(2), 57(100), 41(22), 29(29).
Woody-orris odor.

33. 7-Methylene-9,9-dimethyl-dec-4-yn-3-ol

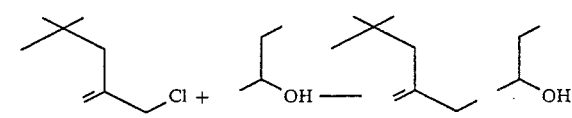

IR: 3350, 3080, 2250, 1640, 900 cm$^{-1}$;
NMR: 0.92 (9H, s); 2.0 (2H, s); 3.0 (2H, s); 4.21–4.55 (H, m); 4.81(s) and 5.25(m) (2H) δ ppm;
MS: M$^+$=194(0.1); m/e: 179(1), 161(4), 147(1), 133(1), 120(21), 105(34), 91(11), 79(14), 69(1), 57(100), 41(27), 29(23).
Multiodorant compound.

The invention is better illustrated by the following examples.

EXAMPLE 1

100 Grams of soap chips prepared by chopping a bar of commercial soap (origin: Procter & Gamble, Cincinnati, Ohio USA) were mixed with 1 g of 5,7,7-trimethyloctyl propionate until a homogeneous mass was obtained. The usual treatment of this mass consisted in melting it by applying a gentle heat. After cooling, the soap mass was cut into bars which were subjected to a fragrance evaluation. The panel of experts declared that the soap possessed a fruity character of pear-type.

EXAMPLE 2

A cologne for children was prepared by mixing the following ingredients (parts by weight):

| Sweet orange oil | 400 |
|---|---|
| Lemon oil | 300 |
| Bergamot oil | 100 |
| Neroli Bigarade | 50 |
| synth. lavender oil | 30 |
| Synth. bulgarian rose oil | 20 |
| | 900 |

By adding to 90 g of the above base composition 10 g of 5,7,7-trimethyloctylpropionate, a novel composition resulted where sweet and fruity fragrance was more marked than that of the base composition.

EXAMPLE 3

A base perfume composition of "green-apple" type was prepared by mixing the following ingredients (parts by weight):

| α-Damascone 10%*[1] | 300 |
|---|---|
| Jasmonacetal | 200 |
| cis-o-tert-Butylcyclohexyl-acetal | 200 |
| Ethylene-brassylate | 50 |
| Geranylacetone | 40 |
| Phenylethanol | 30 |
| β-Damascone 1%*[1] | 20 |
| Veloutone[1][2] | 20 |
| Ethylacetoacetate | 20 |
| trans-2-Hexenol 10%* | 10 |
| | 890 |

*in diethyl phthalate
[1]origin: Firmenich SA
[2]trimethyl-pentyl-cyclopentanone A novel composition was prepared by adding 11 g of 5,7,7-trimethyloctyl propionate to 89 g of the above base composition. This novel composition possessed more harmony and a note of ripe apple that conferred a pleasant character to the base composition making it particularly suitable to perfume shampoos and soaps.

What we claim is:
1. 5,7,7-Trimethyloctyl propionate.
2. A process to confer, improve or modify the fragrance properties of perfumes or perfumed products, which comprises the step of adding thereto a fragrance modifying quantity of the compound of claim 1.
3. A perfume composition containing as an active ingredient about 1% to 30% by weight of the compound of claim 1.

* * * * *

UNITED STATES PATENT AND TRADEMARK OFFICE
CERTIFICATE OF CORRECTION

PATENT NO. : 4,525,298

DATED : June 25, 1985

INVENTOR(S) : Karl H. Schulte-Elte and Bernard L. Muller

It is certified that error appears in the above-identified patent and that said Letters Patent is hereby corrected as shown below:

Column 1, lines 10-15, the structural formula (1) should be:

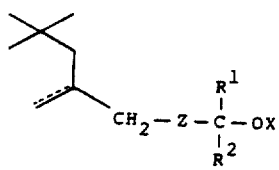

Column 2, line 18, "peak-like" should be -- pear-like --.

Column 2, lines 41-47, the structural formula (1) should be:

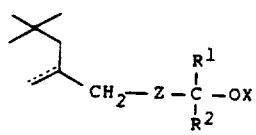

Column 3, lines 6, 13, 27 and 31, the symbols immediately following X are "equals signs".

UNITED STATES PATENT AND TRADEMARK OFFICE
CERTIFICATE OF CORRECTION

PATENT NO. : 4,525,298

DATED : June 25, 1985

INVENTOR(S) : Karl H. Schulte-Elte and Bernard L. Muller

It is certified that error appears in the above-identified patent and that said Letters Patent is hereby corrected as shown below:

Column 6, lines 48-53, the structural formula should be:

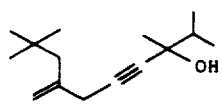

Column 7, lines 1-5, the structural formula should be:

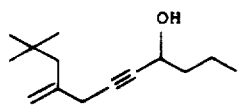

Column 7, lines 25-29, the structural formula should be:

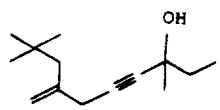

UNITED STATES PATENT AND TRADEMARK OFFICE
CERTIFICATE OF CORRECTION

PATENT NO. : 4,525,298

DATED : June 25, 1985

INVENTOR(S) : Karl H. Schulte-Elte and Bernard L. Muller

It is certified that error appears in the above-identified patent and that said Letters Patent is hereby corrected as shown below:

Column 8, lines 21-31, the structural formulas should be:

Column 8, lines 41-51, the structural formulas should be:

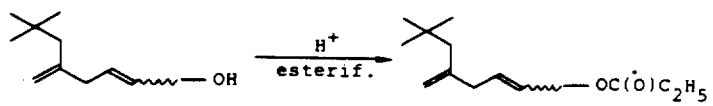

Column 8, lines 63-67, and column 9, lines 1-7, the structural formulas should be:

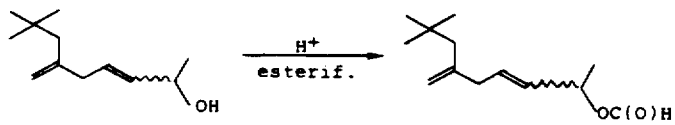

UNITED STATES PATENT AND TRADEMARK OFFICE
CERTIFICATE OF CORRECTION

PATENT NO. : 4,525,298
DATED : June 25, 1985
INVENTOR(S) : Karl H. Schulte-Elte and Bernard L. Muller It is certified that error appears in the above-identified patent and that said Letters Patent is hereby corrected as shown below:

Column 9, lines 20-31, the structural formulas should be:

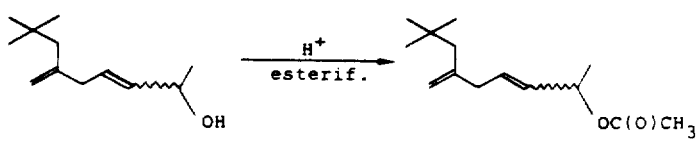

Column 9, lines 45-56, the structural formulas should be:

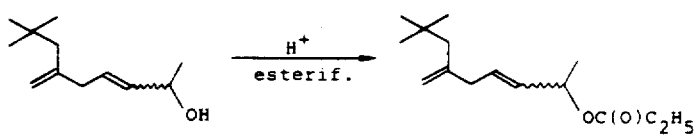

Column 10, lines 1-7, the structural formula should be:

UNITED STATES PATENT AND TRADEMARK OFFICE
CERTIFICATE OF CORRECTION

PATENT NO. : 4,525,298
DATED : June 25, 1985
INVENTOR(S) : Karl H. Schulte-Elte and Bernard L. Muller It is certified that error appears in the above-identified patent and that said Letters Patent is hereby corrected as shown below:

Column 10, lines 33-37, the structural formula should be:

Column 11, lines 1-6, the structural formula should be:

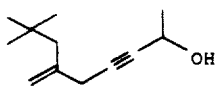

Column 11, lines 36-40, the structural formula should be:

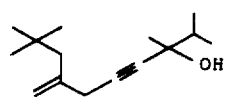

UNITED STATES PATENT AND TRADEMARK OFFICE
CERTIFICATE OF CORRECTION

PATENT NO. : 4,525,298

DATED : June 25, 1985

INVENTOR(S) : Karl H. Schulte-Elte and Bernard L. Muller

It is certified that error appears in the above-identified patent and that said Letters Patent is hereby corrected as shown below:

Column 12 lines 1-7, the structural formula should be:

Column 12, lines 38-43, the structural formula should be:

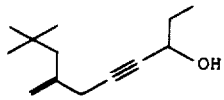

Column 12, line 60, "22. 7-Methylene-9,9-dimethyl-3-ethyl-" should be moved to line 61, before "dec-4-en-3-ol".

Column 12, lines 63-68, the structural formula should be:

UNITED STATES PATENT AND TRADEMARK OFFICE
CERTIFICATE OF CORRECTION

PATENT NO. : 4,525,298
DATED : June 25, 1985
INVENTOR(S) : Karl H. Schulte-Elte and Bernard L. Muller It is certified that error appears in the above-identified patent and that said Letters Patent is hereby corrected as shown below:

Column 13, line 16, "23. 5-Methylene-" should be moved to line 17 before "7,7-dimethyl-oct-2-yn-1-yl propionate".

Column 13, lines 18-28, the structural formulas should be:

Column 13, lines 39-48, the structural formulas should be:

Column 13, lines 58-67, the structural formulas should be:

UNITED STATES PATENT AND TRADEMARK OFFICE
CERTIFICATE OF CORRECTION

PATENT NO. : 4,525,298

DATED : June 25, 1985

INVENTOR(S) : Karl H. Schulte-Elte and Bernard L. Muller

It is certified that error appears in the above-identified patent and that said Letters Patent is hereby corrected as shown below:

Column 14, lines 9-13, the structural formulas should be:

Column 14, lines 23-33, the structural formulas should be:

Column 14, lines 43-53, the structural formulas should be:

UNITED STATES PATENT AND TRADEMARK OFFICE
CERTIFICATE OF CORRECTION

PATENT NO. : 4,525,298

DATED : June 25, 1985

INVENTOR(S) : Karl H. Schulte-Elte and Bernard L. Muller

It is certified that error appears in the above-identified patent and that said Letters Patent is hereby corrected as shown below:

Column 14, lines 63-68, and Column 15, lines 1-6, the structural formulas should be:

Column 15, lines 17-26, the structural formulas should be:

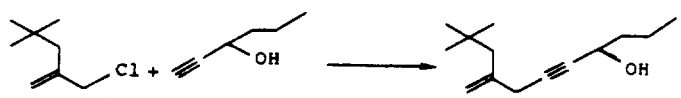

Column 15, lines 36-40, the structural formulas should be:

UNITED STATES PATENT AND TRADEMARK OFFICE
CERTIFICATE OF CORRECTION

PATENT NO. : 4,525,298

DATED : June 25, 1985

INVENTOR(S) : Karl H. Schulte-Elte and Bernard L. Muller

It is certified that error appears in the above-identified patent and that said Letters Patent is hereby corrected as shown below:

Column 15, lines 51-60, the structural formulas should be:

Column 16, lines 3-7, the structural formulas should be:

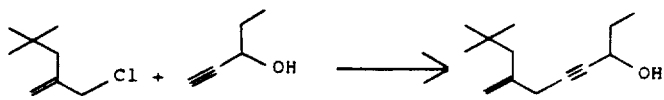

Signed and Sealed this

Seventh Day of January 1986

[SEAL]

Attest:

DONALD J. QUIGG

Attesting Officer

Commissioner of Patents and Trademarks